United States Patent [19]
Cherkas et al.

[11] Patent Number: 5,858,494
[45] Date of Patent: Jan. 12, 1999

[54] FISHING LURE DECALS

[76] Inventors: Ronald D. Cherkas, 2339 NW. 78th Ave., Ankeny, Iowa 50317; Billy E. Echart, 201 Flenniken, Gladewater, Tex. 75647

[21] Appl. No.: 621,213

[22] Filed: Mar. 22, 1996

[51] Int. Cl.⁶ ................ A61F 13/02; B32B 3/00
[52] U.S. Cl. .......... 428/40.1; 428/77; 428/174; 428/195; 428/411.1; 283/81; 427/316
[58] Field of Search .............. 427/316; 283/81; 428/195, 40.1, 77, 174, 411.1

[56] References Cited

U.S. PATENT DOCUMENTS

| | | | |
|---|---|---|---|
| 3,779,748 | 12/1973 | Mosehauser et al. | 96/1 R |
| 4,335,495 | 6/1982 | Buchanan | 29/428 |
| 4,492,054 | 1/1985 | Barnhart | 43/42.23 |
| 4,589,222 | 5/1986 | Barnhart | 43/42.23 |
| 4,759,982 | 7/1988 | Jenssen et al. | 428/343 |
| 5,098,772 | 3/1992 | Strom | 428/211 |
| 5,411,295 | 5/1995 | Bates et al. | 283/81 |
| 5,520,958 | 5/1996 | Doesburg et al. | 427/316 |

*Primary Examiner*—William Krynski
*Assistant Examiner*—Cathy F. Lam
*Attorney, Agent, or Firm*—Kent A. Herink, Esq.

[57] ABSTRACT

A decal allowing a fisherman to customize a fishing lure. The decal is printed with a life-like image of a fish on one side and the decal has an adhesive on the other side. Initially, the decal is present on a substrate. When a fisherman peels the decal from the substrate, some or all of an adhesive stays on the decal allowing the fisherman to attach the decal to a fishing lure. The image on the decal is waterproof and the decal may be applied to many different lures including spinner bait lures, blades and crank bait lures. The decal may have a scent or flavor enhancer in the waterproofing overcoat, in the ink used to create the image on the decal, in the adhesive, or in all three. Additionally, rattle eyes may be provided on the fishing lure.

7 Claims, 4 Drawing Sheets

FISHING LURE DECALS

BACKGROUND OF THE INVENTION

The present invention relates generally to fishing lures and, more specifically, to decals designed to be applied to the lure by the fisherman.

Among the strategies used by fishermen in attempting to catch fish is the use of fishing lures. Typically, a fisherman has a tackle box which contains many lures having different appearances so that the fisherman may use different lures depending on the season, the time of day, the weather, or any other such factors which affects the success or failure of a given lure at a given time. For example, if a fisherman is out fishing and a factor such as the weather changes or it goes from day to night, the fisherman will change lures. This is because certain lures work better under certain conditions. Frequently, if a fisherman is out fishing and not having success with a given fishing lure, the fisherman will change lures. Consequently, fishermen have been forced to remove the old lure and attach the new lure on a fairly frequent basis in order to maximize the success rate of catching fish in a given outing.

SUMMARY OF THE INVENTION

The present invention consists of a decal designed to be applied to the lure by the fisherman. The decal allows the fisherman to place the decal on a lure, thus changing the appearance of the lure without removing the lure from the fishing line. By having a sheet of many decals, a fisherman is able to change the appearance of his lure many times without overloading his tackle box with many different looking lures. Printed on each decal is an image of a fish or other bait creature. The decal is flexible, thus allowing the fisherman to shape the decal onto the lure. Also, the image which is printed on the decal is waterproof. The decal may be designed to be applied to any of a multitude of different types of lures including spinner bait lures, blades and crank bait lures. A scent and/or flavor enhancer may be provided on or in a waterproofing overcoat, the image on the decal, or an adhesive which is on the back side of the decal. The scent or flavor enhancer also works to make the lure more attractive to the fish that the fisherman is trying to catch.

The object of the present invention is to provide a decal which allows a fisherman to customize his fishing lure.

Another object of the invention is to provide a decal which can be applied to the fishing lure by the fisherman where the decal includes a life-like image of a fish which increases the success rate of the fishing lure.

Still another object of the invention is to provide a decal which includes a stochastic printed image.

A further object of the invention is to provide a fishing lure having a scent or flavor enhancer which makes the fishing lure more attractive to fish.

DETAILED DESCRIPTION OF A PREFERRED EMBODIMENT

Figure 1:
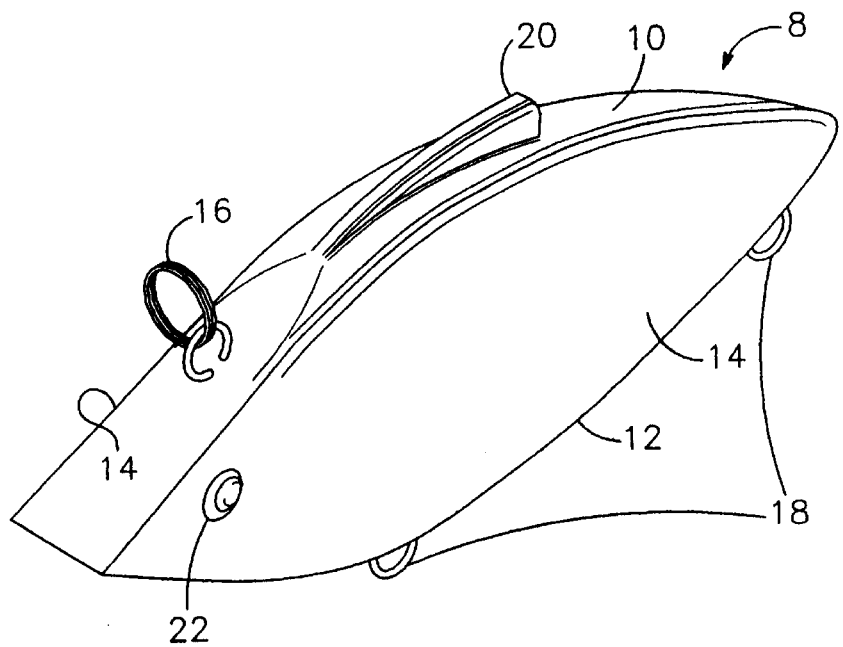
FIG. 1 is a perspective view of a fishing lure.

Fishermen use many different techniques in attempting to catch fish. One of the techniques is the use of fishing lures. Generally a fisherman casts a lure into the water and slowly reels in the lure hoping that a fish attacks the lure and gets hooked on hooks which depend from the lure. Thereafter, the fisherman reels in the lure and a fish is successfully caught. Typically, lures come in many different shapes, sizes, and colors. Generally a fisherman chooses the lure based on a number of factors. The decisive factors can include: the time of day, the weather, the naturally occurring foods being eaten by the fish, and which species of fish the fisherman is attempting to catch. Because certain lures work better under certain circumstances, typically a fisherman has a tackle box which contains many different lures. The present invention is geared to enable the fisherman to effectively fish with a lesser number of lures.

The invention is a decal which can be removed from a substrate and attached to an existing fishing lure. The decal is generally a vinyl strip; however, other comparable flexible materials may be used. On one side of the strip is an adhesive which allows a fisherman to peel the decal off a substrate and, because some or all of the adhesive remains on the strip when the decal is removed from the substrate, attach the decal to a fishing lure. The adhesive is one which allows the decal to remain adhered to the lure even though the lure comes into contact with water. On the other side of the decal, there is printed an image, preferably of a fish or another bait creature. To this end, actual species of fish can be photographed with a digital camera, or a digital scanner may be used in order to create a computer generated image which is either two dimensional or three dimensional. Thereafter, the image may be printed or otherwise formed onto the decal. Printing may be done by a variety of methods including inkjet, electrostatic, four-color offset, and silk-screening as well as photoprinting or stochastic printing. After the image is created on the decal, the image, if not waterproof already, can be coated with a substance which makes the image waterproof. A suitable substance which may be used to overcoat the image may be lacquer; however, other such materials may be used. Preferably, the lacquer has a shiny or glittery material included in order to create an overall appearance in the lure which is more attractive to fish. The decals may be provided on a sheet making the selection among many different decals easier for the fisherman. Additionally, the decal may be a large sheet containing many different images whereby a fisherman can cut a smaller decal from the sheet in the shape of the fishing lure which the fisherman is using. This would allow the fisherman to choose from a wide variety of images which may be contained on the sheet, and would allow the fisherman to apply the decal to any lure notwithstanding the unique shape of the lure. The decals may be used on many different types of lures including spinner bait lures, blades and crank bait lures. As an option, a scent or flavor enhancer may be used to make the resulting lure more attractive to fish. The scent or flavor enhancer may be applied through the waterproofing overcoat, through the ink used to create the image, through the adhesive, or all of the above. Finally, rattle eyes may be provided on the lure which create a more life-like appearance and would more readily attract a fish to the lure.

Referring to the drawings, there is illustrated in FIG. 1 a general depiction of a fishing lure 8. The lure 8 is generally shaped like a fish, having a top portion 10, a bottom portion 12 and side portions 14. On the top portion 10 of the lure 8 is an eyelet 16 for receiving a fishing line (not shown). Generally, on the bottom 12 of the lure 8 is one or more eyelets 18 for receiving the top end of a hook (not shown) so that the hook depends from the lure 8 and hooks the fish when the fish attempts to eat the lure 8. The top portion 10 of the lure 8 also has a fin 20 which assists in guiding the lure 8 through the water and keeps the lure 8 in an upright position. Also assisting in the maintenance of the upright position of the lure 8 as the lure 8 guides through the water are the weight of the hooks which depend from the bottom 12 of the lure 8 at the eyelets 18. The lure 8 has an eye 22 on each side 14 of the lure 8 which may be "rattle eyes" where a rattle eye is a hollow, clear bubble with a floating black disc.

Figure 2:
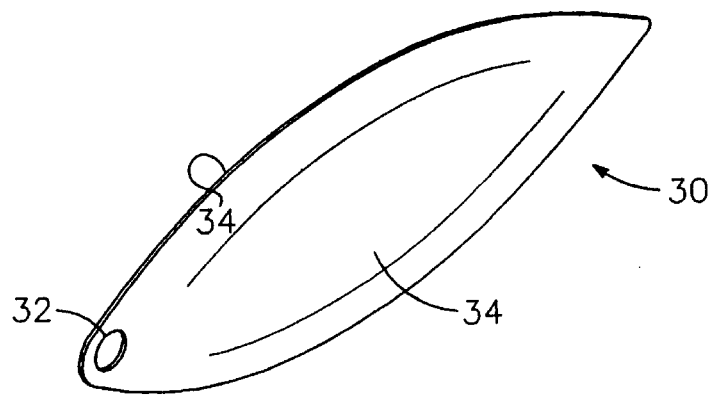
FIG. 2 is a perspective view of a blade.

FIG. 2 illustrates a blade 30. The blade 30 has an eyelet 32 for tying the blade 30 to the fishing line (not shown). The blade 30 is generally flat having two sides 34, and having an oblong fish-like shape.

Figure 3:
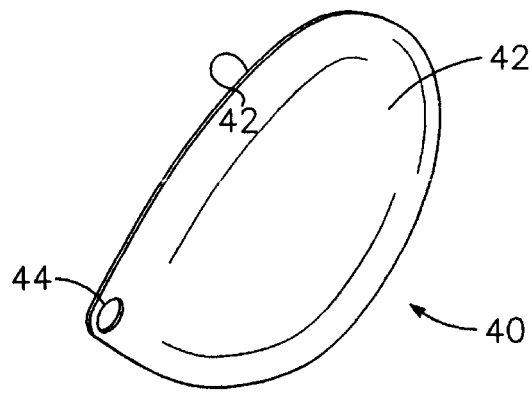
FIG. 3 is a perspective view of a blade.

FIG. 3 is another blade 40 having a less oblong shape and generally depicting the shape of a different species of fish as that depicted by the shape of the blade in FIG. 2. Blade 40 is also flat having basically two sides 42 and an eyelet 44 for tying a fishing line (not shown) to the blade 40.

Figure 4:
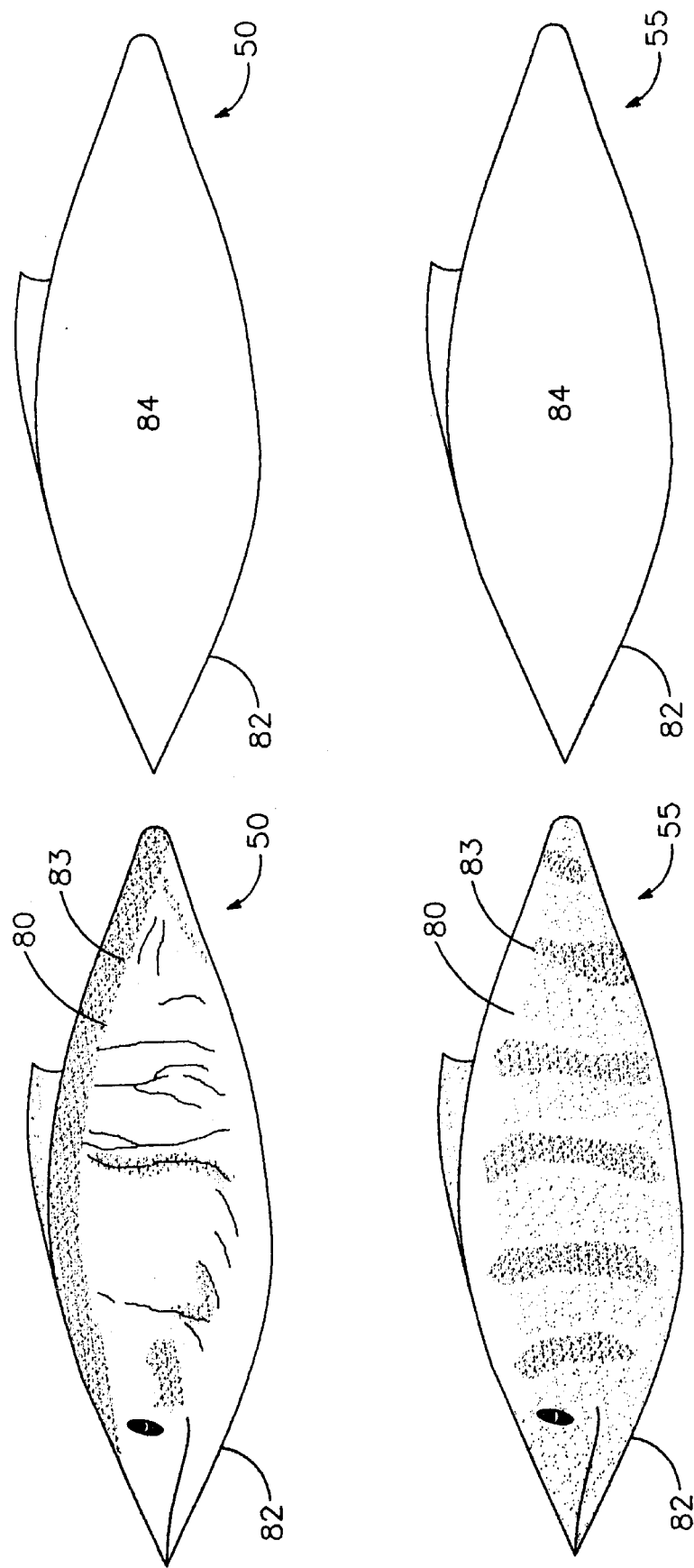
FIGS. 4, 5, & 6 are a group of graphic representations of decals.
Figure 5:
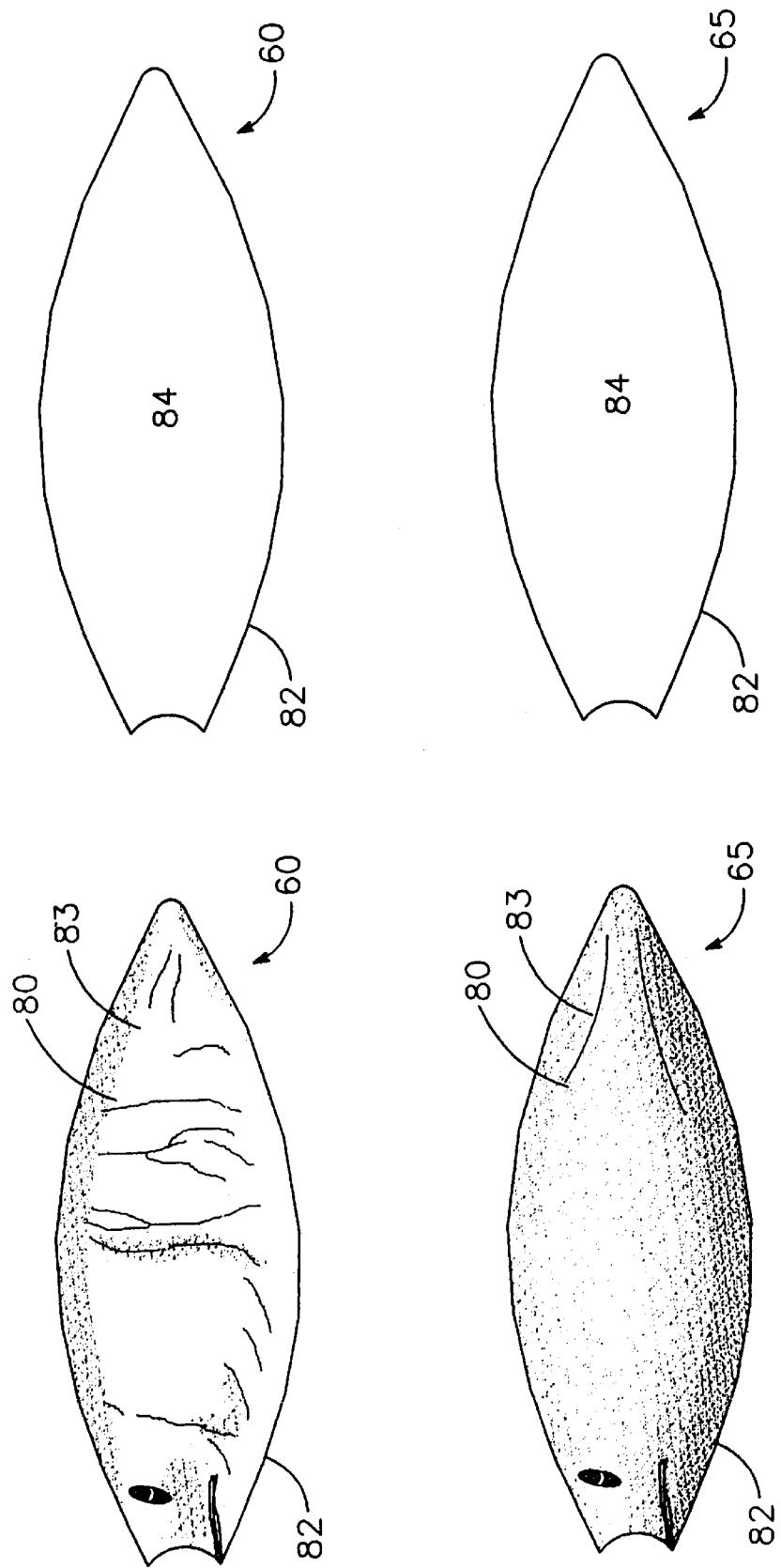
Figure 6:
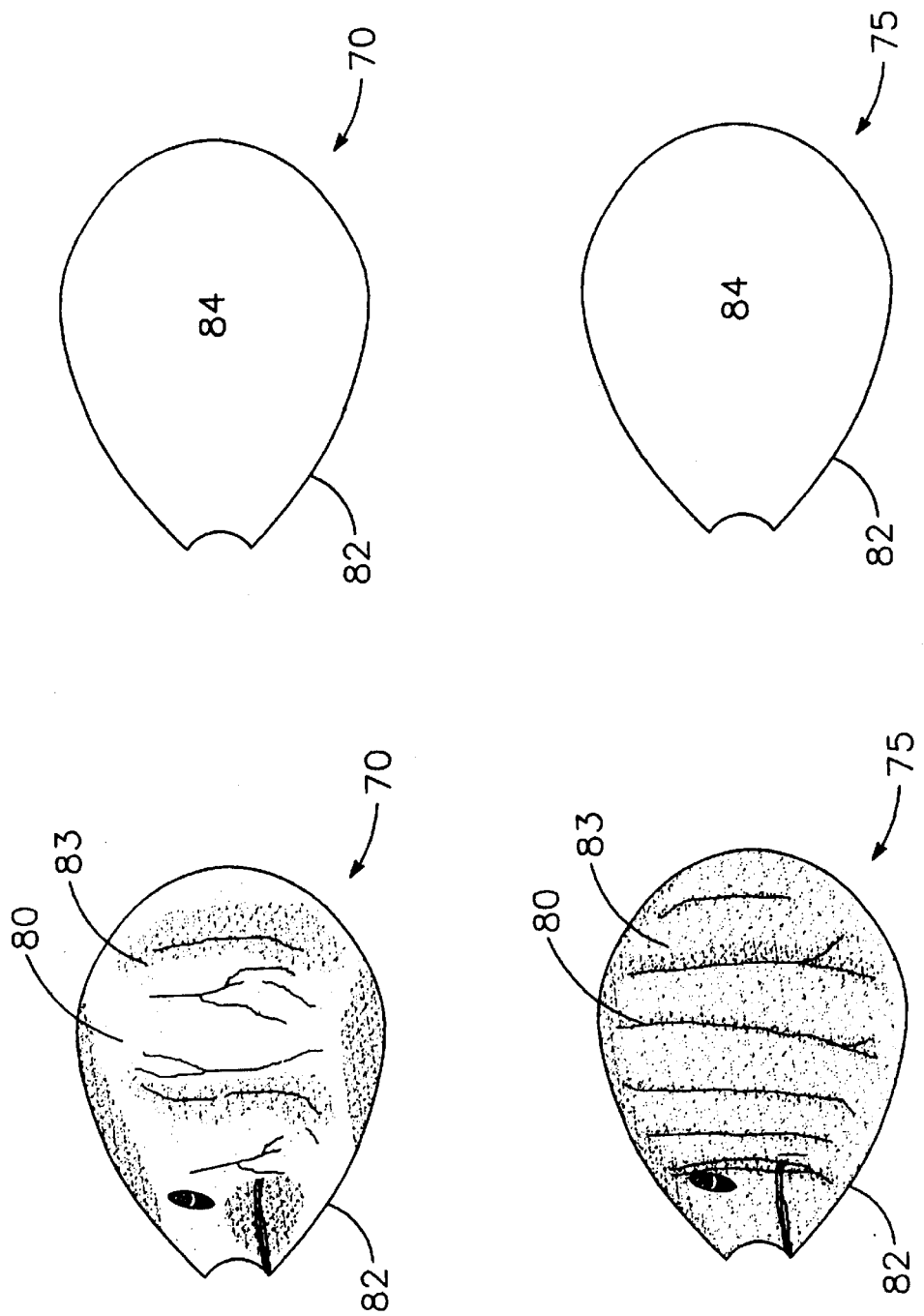

FIG. 4 is an illustration of two different decals 50 and 55 which may be attached to the sides 14 of the lure 8 depicted in FIG. 1. Depicted in FIG. 5 are decals 60 and 65 which may be attached to the sides 34 of the blade 30 of FIG. 2. Additionally, FIG. 6 depicts decals 70 and 75 which may be applied to the sides 42 of the blade 40 shown in FIG. 3. Each decal in FIGS. 4, 5, and 6 includes a life-like image 80 of a species of fish. Optionally, a decal may include an image of some other bait creature. In the preferred embodiment, each decal is made by taking a vinyl strip 82; however, other materials may be appropriate as would be known to one ordinarily skilled in the art, and printing the image 80 on a side 83 of the strip 82 using one or more different methods. The methods which, among others, may be used to print the image 80 on the strip 82 are: inkjet printing, electrostatic printing, four color offset printing, silk screen printing, as well as stochastic printing or using a photo print process. The image 80 may be one obtained from a digital camera or a digital scanner from an actual species of fish. The image 80 may be generated as a two dimensional or three dimensional image. Also, the image 80 may be shiny or glittery or may have any other effect which may be determined to be attractive to fish. On the opposite side 84 of each vinyl strip 82 is an adhesive. Any adhesive may be provided. However, on the preferred embodiment, the adhesive is one which allows a fisherman to peel the decal off a substrate (not shown), and when the decal is removed from the substrate, the adhesive, or a substantial part thereof, remains on the side 84 of the decal. Also, in the preferred embodiment, the adhesive is waterproof to the extent that when the lure having a decal attached comes into contact with water, the decal remains substantially secured to the side of the lure. Thereafter, the fisherman can apply the side 84 of the decal to the corresponding side 14 of the fishing lure 8, to the corresponding side 34 of blade 30, or to the corresponding side 42 of blade 40. In the preferred embodiment, the image 80 on the side 83 of the strip 82 is coated with a substance which makes the image waterproof. However, one skilled in the art would realize that it is possible to provide a waterproof image without overcoating the image with some substance. Nevertheless, a suitable substance which may be used to waterproof the image may be lacquer; however, one skilled in the art should recognize that there are other suitable substances to apply to the image which would result in the image being waterproof. Each decal may be provided with a scent or flavor enhancer which appeals to the live fish that the fisherman is trying to catch with the lure. The scent or flavor enhancer may be provided to the decal through the waterproofing overcoat, through the ink used to create the image 80 on the decal, through the adhesive present on the side 84 of the decal, or all of the above. To make the lure even more attractive to fish, rattle eyes may be provided wherein the eyes of the lure consist of two hollow, clear bubbles with each bubble containing a floating black disc.

In operation, a fisherman would be provided with one or more decals adhered to a substrate. The fisherman would peel the decal off the substrate and all or a portion of the adhesive would remain on the side 84 of the decal as the decal is removed from the substrate. The fisherman would then attach the side 84 of the decal to the side 14 of the lure 8, to the side 34 of blade 30, to the side 42 of blade 40, or to some other lure or blade. The fisherman would attach the side 84 of the decal which has the waterproof adhesive onto the fishing lure, thus allowing the other side 83 of the decal which contains the image 80 to be in view as one looks at the lure. The fisherman may use a complimentary decal on the other side 14 of the lure such that the lure as a whole would appear to be a fish having a logical head and tail. However, the fisherman may use many different decals upon a single lure, may use a decal having a certain appearance for one side of the lure and may use a decal having a completely different appearance on the other side of the lure, or may use only one decal on a given lure. Also, the decal may be provided in the form of a large sheet allowing the fisherman to cut from the sheet the shape of decal that the fisherman desires to apply to any given lure and the large image provided on the sheet may be an image containing many different colors and effects such as a glittery effect, a shiny effect or a three dimensional effect allowing the fisherman to further customize his lure by cutting the desired decal from the sheet and applying the decal to any given lure. The fisherman would then cast or lower the lure into the water and the lure would create the appearance of being a fish in the water. Then, the lure would attract a fish and the fisherman would be successful in his attempt to catch fish. If the decal is provided with a scent or flavor enhancer, this would further increase the chances of successfully catching a fish by using the lure. Moreover, if a three dimensional printing process is used on the decals, a parallax would appear in the water as the lure moves through the water. This is true especially if the lure is rolling or pitching as it moves through the water.

Although the invention has been described with respect to a preferred embodiment thereof, it is to be also understood that it is not to be so limited since changes and modifications can be made therein which are within the full intended scope of this invention as defined by the appended claims.

We claim:

1. A fishing lure capable of having its appearance changed upon securement of a flexible member carrying an image of a portion of a bait to a side of the fishing lure, said lure comprising:

a) a side;

b) a flexible panel having a first side and an opposite, second side, the first side of the panel being releasably secured to the side of the lure by a substantially waterproof adhesive between the first side of the panel and the side of the lure, and said adhesive being capable of substantially maintaining a securement between the side of the lure and the first side of the strip upon the lure coming into contact with water; and c) a waterproof image of a portion of a bait on the second side of the panel.

2. The lure as defined in claim 1, wherein said flexible panel is comprised of vinyl.

3. The lure as defined in claim 1, wherein the image is printed using a method selected from the group consisting of ink jet, electrostatic, four-color offset, silk-screening, photoprinting, and stochastic printing.

4. The lure as defined in claim 1, wherein the image is coated with a lacquer overcoat.

5. The lure as defined in claim 4, wherein the overcoat contains an enhancer.

6. The lure as defined in claim 1, wherein the adhesive contains an enhancer.

7. The lure as defined in claim 1, wherein the image contains an enhancer.

* * * * *